(12) United States Patent
Ding et al.

(10) Patent No.: US 11,622,939 B2
(45) Date of Patent: Apr. 11, 2023

(54) HS-25 TABLET AND PREPARATION METHOD THEREFOR

(71) Applicant: ZHEJIANG HISUN PHARMACEUTICAL CO., LTD., Zhejiang (CN)

(72) Inventors: Li Ding, Zhejiang (CN); Jun Dai, Zhejiang (CN); Chunrong Feng, Zhejiang (CN); Changliang Dai, Zhejiang (CN)

(73) Assignee: ZHEJIANG HISUN PHARMACEUTICAL CO., LTD., Zhejiang (CN)

( * ) Notice: Subject to any disclaimer, the term of this patent is extended or adjusted under 35 U.S.C. 154(b) by 194 days.

(21) Appl. No.: 16/766,292

(22) PCT Filed: Nov. 23, 2018

(86) PCT No.: PCT/CN2018/117086
§ 371 (c)(1),
(2) Date: May 22, 2020

(87) PCT Pub. No.: WO2019/101150
PCT Pub. Date: May 31, 2019

(65) Prior Publication Data
US 2021/0145754 A1    May 20, 2021

(30) Foreign Application Priority Data

Nov. 23, 2017 (CN) .............................. 201711183388

(51) Int. Cl.
*A61K 9/20* (2006.01)
*A61K 9/00* (2006.01)
*A61K 31/397* (2006.01)

(52) U.S. Cl.
CPC .......... *A61K 9/2059* (2013.01); *A61K 9/0056* (2013.01); *A61K 9/2018* (2013.01); *A61K 9/2027* (2013.01); *A61K 9/2054* (2013.01); *A61K 9/2095* (2013.01); *A61K 31/397* (2013.01)

(58) Field of Classification Search
None
See application file for complete search history.

(56) References Cited

U.S. PATENT DOCUMENTS

2008/0275020 A1* 11/2008 Moore ................. A61K 9/2018
514/460
2012/0208994 A1   8/2012 Bai et al.
2015/0218091 A1   8/2015 Wei et al.

FOREIGN PATENT DOCUMENTS

| CN | 101993403 A | 3/2011 | |
|---|---|---|---|
| CN | 103655453 A | 3/2014 | |
| CN | 104490833 A | 4/2015 | |
| WO | WO-2009074286 A3 * | 7/2009 | ........... A61K 31/397 |
| WO | 2011017907 A1 | 2/2011 | |
| WO | 2014036956 A1 | 3/2014 | |

OTHER PUBLICATIONS

International Search Report for PCT/CN2018/117086 dated Jan. 24, 2019, ISA/CN.

* cited by examiner

*Primary Examiner* — Susan T Tran
(74) *Attorney, Agent, or Firm* — Yue (Robert) Xu (57) ABSTRACT

An HS-25 tablet, an HS-25 solid dispersion composition, a preparation method therefor and usage thereof. The HS-25 tablet is made by using HS-25 and excipients for wet granulation, drying, granulating and tablet pressing.

28 Claims, 2 Drawing Sheets

HS-25 TABLET AND PREPARATION METHOD THEREFOR

CROSS REFERENCE

This application is the national phase of International Application No. PCT/CN2018/117086, titled "HS-25 TABLET AND PREPARATION METHOD THEREFOR", which claims the priority of Chinese Patent Application No. 201711183388.3, filed to the China National Intellectual Property Administration on Nov. 23, 2017, and titled "hyzetimibe tablet and preparation method thereof", the content of which is incorporated herein by reference in its entirety.

FIELD

The present disclosure belongs to the field of medicines, and particularly relates to a hyzetimibe (HS-25) tablet and preparation method thereof.

BACKGROUND

Hyzetimibe is a cholesterol-lowering drug, disclosed in WO2011017907, and has a structural formula of:

Hyzetimibe reduces absorption of cholesterol and phytosterol as well as reabsorption of bile cholesterol by inhibiting the cholesterol-absorbing protein NPC1L1 on the intestinal epithelial cells, thereby reducing sterol level in plasma. It is clinically used for the treatment of: 1. primary hypercholesterolemia; 2. homozygous familial hypercholesterolemia (HoFH); and 3. homozygous sitosterolemia (or phytosterolemia).

The hyzetimibe bulk drug has a strong electrostatic adsorption, resulting in a poor fluidity; and has a poor solubility in water and a poor absorption in the body. Moreover, this compound is sensitive to temperature and humidity. Due to the above-mentioned problems in stability and absorption of hyzetimibe, it is necessary to adopt a suitable preparation process to prepare hyzetimibe into a formulation which is stable and well-absorbed in the body.

Hyzetimibe is a poorly soluble drug and thus in order to improve bioavailability of the drug in the body, an appropriate amount of surfactant such as Tweens or sodium dodecyl sulfate can usually be added into formulations. In the tablet prescription of the present invention, sodium dodecylsulfate can be added as a surfactant. Because hyzetimibe is unstable under alkaline conditions, the amount of sodium dodecyl is generally controlled below 5% by weight of the tablet.

Micronization of a bulk drug is a common method for improving drug dissolution and increasing drug bioavailability. However, due to the strong electrostatic adsorption of the hyzetimibe bulk drug, if the particle size of the micronized bulk drug is too small, the electrostatic adsorption will be intensified and thus the contact area with moisture and air will be increased, resulting in an unstable product; or otherwise, if the particle size is too large, a slow final product dissolution and a low bioavailability would be caused. The present disclosure provides a suitable particle size range of the bulk drug, within which the hyzetimibe bulk drug has a strong processability, and the final product prepared therefrom has a good bioavailability, stable crystal form and related substances, and thus a good commercial production value.

Using solid dispersion technology is another method to improve the bioavailability of poorly soluble drugs. However, this technology is at risk of possibly transforming the crystal form of a drug, from a high-energy state amorphous form to a stable crystal form. This may pose a potential damage to the stability and solubility of drugs.

Hyzetimibe tablets prepared by aqueous granulation without addition of an antioxidant in prescription are stable under long-term accelerated storage conditions. However, for hyzetimibe tablets prepared by ethanol granulation without addition of an antioxidant in prescription, impurities increase faster, mainly because hyzetimibe in an amorphous form has a higher energy and a larger probability to contact with moisture and oxidant substances in formulations, and thus are easily degraded under the influence of temperature. In the present disclosure, by adding an appropriate amount of an antioxidant such as butylated hydroxytoluene in the aqueous or organic solvent prescription, degradation into impurities can be effectively decreased. Adding an appropriate amount of butylated hydroxytoluene in hyzetimibe tablets contributes to the stability of the product, and the amount added thereof can be adjusted according to the process.

This patent application describes a wet granulation process for hyzetimibe tablets in detail, whereby, independent of aqueous or ethanol granulation, the prepared tablets are smooth and clean in appearance, are released quickly in vitro, are qualified in content and content uniformity, do not exceed limit requirements for degradation into impurities, are stable in crystal form and are simple in the production process, thereby solving the related difficulties in industrial production.

SUMMARY

In order to solve the above technical problems, the present disclosure provides a hyzetimibe tablet and preparation method therefor. Such a tablet has advantages such as a high bioavailability, a good stability, a high yield, and being easy for commercially manufacturing.

The hyzetimibe tablet according to the present disclosure comprises hyzetimibe, a filler, a binder, a disintegrating agent, and a lubricant, wherein hyzetimibe accounts for 1-20% by weight of the tablet. The hyzetimibe tablet preferably further comprises a stabilizer and/or surfactant.

Preferably, the filler is at least one of lactose, microcrystalline cellulose and pregelatinized starch; preferably, at least one of lactose and microcrystalline cellulose; and more preferably, at least one of 30-60% by weight of lactose and 20-60% by weight of microcrystalline cellulose.

Preferably, the binder is at least one of hydroxypropyl cellulose and povidone; preferably, povidone; more preferably, 1-5% by weight of povidone; and most preferably, 1-5% by weight of povidone K30.

Preferably, the disintegrating agent is at least one of crospovidone and croscarmellose sodium; and preferably, 1-10% by weight of crospovidone or 1-10% by weight of croscarmellose sodium.

Preferably, the stabilizer is at least one of butylated hydroxyanisole and butylated hydroxytoluene; preferably, butylated hydroxytoluene; and more preferably, 0.005-0.1% by weight of butylated hydroxytoluene.

Preferably, the surfactant is at least one of sodium dodecylsulfate and polysorbate; preferably, sodium dodecylsulfate; and more preferably, 1-5% by weight of sodium dodecylsulfate.

Preferably, the lubricant is at least one of magnesium stearate and talc; preferably, magnesium stearate; and more preferably, 0.5-2% by weight of magnesium stearate.

The hyzetimibe tablet can be prepared by granulating using water, alcohol, acetone or a similar solvent, or a mixture thereof, and then tabletting.

After a number of experiments, the inventor has surprisingly discovered that: by dissolving hyzetimibe in an organic solvent containing povidone, and then pouring or spraying into adjuvants thereby preparing a solid dispersion thereof. By doing this, not only the problem of electrostatic adsorption of the bulk drug can be solved, but also the crystal form transformation can be inhibited at the same time.

Based on this finding, in one aspect, the present disclosure provides a hyzetimibe solid dispersion composition comprising hyzetimibe and povidone.

In another aspect, the present disclosure provides a hyzetimibe tablet comprising the hyzetimibe solid dispersion composition of the present disclosure.

In yet another aspect, the present disclosure further provides the use of the hyzetimibe solid dispersion composition of the present disclosure in the manufacture of hyzetimibe solid formulations. The solid formulation is preferably selected from the group consisting of tablet, capsule, granule and powder.

The present disclosure also provides a method for preparing the hyzetimibe solid dispersion composition of the present disclosure, comprising the following step: dissolving hyzetimibe in an organic solvent comprising povidone. In some specific embodiments, the method for preparing the hyzetimibe solid dispersion composition optionally further comprises the steps of: pouring or spraying the hyzetimibe solution obtained in the above step into adjuvants, and optionally sizing and/or drying. The organic solvent can be selected from the group consisting of alcohols, ethers, ketones, esters and the like, including but not limited to methanol, ethanol, propanol, isopropanol, n-butanol, isobutanol, n-pentanol, isoamyl alcohol, n-hexanol, cyclohexanol, tetrahydrofuran, diethyl ether, methyl ethyl ether, ethyl acetate, ethyl formate, or a mixture thereof. Preferably, the organic solvent is selected from the group consisting of ethanol, isopropanol, and a mixture thereof with water.

The hyzetimibe tablet of the present disclosure can be prepared by a method comprising wet granulating using water and then tabletting. More preferably, the hyzetimibe tablet can be prepared by a method comprising:
(1) mixing hyzetimibe with lactose, microcrystalline cellulose, sodium dodecylsulfate and croscarmellose sodium homogeneously;
(2) dissolving povidone in water;
(3) adding the povidone solution obtained in step (2) into the mixture obtained in step (1), granulating, drying, and sizing; and
(4) mixing the sized particles in step (3) with magnesium stearate homogeneously, and tabletting.

Preferably, hyzetimibe used in the above preparation is hyzetimibe crystal form I.

Preferably, hyzetimibe used in the above preparation has a particle size of 1 μm≤D90≤100 μm, and preferably 1 μm≤D90≤50 μm.

The hyzetimibe tablet of the present disclosure can also be prepared by a method comprising wet granulating using an organic solvent and a solution thereof and then tabletting, wherein the organic solvent and a solution thereof is preferably an alcohol solvent and a solution thereof, more preferably ethanol and a solution thereof, and more preferably an ethanol solution. The hyzetimibe tablet can be prepared by a method comprising:
(1) mixing lactose, microcrystalline cellulose, sodium dodecylsulfate and crospovidone homogeneously, or mixing lactose, microcrystalline cellulose and crospovidone homogeneously;
(2) dissolving hyzetimibe, povidone and butylated hydroxytoluene (BHT) in an alcohol solvent, or dissolving hyzetimibe and povidone in an alcohol solvent;
(3) adding the solution obtained in step (2) into the mixture obtained in step (1), granulating, drying, and sizing; and
(4) mixing the particles obtained in step (3) with magnesium stearate homogeneously, and tabletting.

Preferably, the ethanol solution is an aqueous solution of ethanol, more preferably the concentration of the aqueous solution of ethanol is ≥60% (w/w), more preferably ≥75% (w/w), and most preferably 80-90% (w/w).

Preferably, the ethanol solution is used in an amount of 30-50% (w/w) of prescription amount, and more preferably 35-45% (w/w) of prescription amount.

Preferably, in the preparation method of the present disclosure, the weight ratio of hyzetimibe to povidone is in a range of 10:1 to 1:1, and more preferably 5:1 to 5:3.

Preferably, in the preparation method of the present disclosure, the granulating includes granulating using a high-speed stirring pelletizer or fluidized bed.

Preferably, in the preparation method of the present disclosure, in the hyzetimibe tablet prepared by the method of the present disclosure, more than 90% of hyzetimibe is present in an amorphous form.

The hyzetimibe tablet according to the present disclosure preferably comprises 5-20 mg of hyzetimibe in each dosage unit, and more preferably 5 mg, 10 mg or 20 mg of hyzetimibe in each dosage unit.

Preferably, the hyzetimibe table further comprises in each dosage unit: 20-250 mg of lactose, 20-200 mg of microcrystalline cellulose, 1-10 mg of croscarmellose sodium or 5-30 mg of crospovidone, 1-15 mg of povidone K30, 0-0.2 mg of butylated hydroxytoluene, 0-15 mg of sodium dodecylsulfate, and 0.5-10 mg of magnesium stearate.

The hyzetimibe bulk drug has a strong electrostatic adsorption and poor fluidity; and a poor solubility in water and thus poor absorption in the body. The present disclosure provides two preparation methods for the hyzetimibe tablet. One of the preparation methods comprises: micronizing the hyzetimibe bulk drug and then mixing directly with adjuvants, and then wet granulating using water, to prepare the hyzetimibe tablet, wherein a suitable particle size range is preferred for the bulk drug. The other preparation method comprises the steps of: dissolving the hyzetimibe bulk drug in an organic solvent and preferably in an organic solvent containing povidone, and then optionally pouring or spraying the obtained solution into adjuvants and granulating. Through the above methods, on the one hand, the problem of electrostatic adsorption can be solved, and on the other hand, as a simple solid dispersion technology, bioavailability is advantageously increased and an optimal amount of povidone used is preferred, thereby solving the problem of electrostatic adsorption of the hyzetimibe bulk drug and eliminating the risk of crystal form transformation. The prepared hyzetimibe tablet was still present in an amorphous form during stability test. The preparation method provided by the present disclosure improves bioavailability of hyzetimibe, making it easy to manufacture commercially and offering a high economic value.

DETAILED DESCRIPTION

The present disclosure will be described in detail below in combination with Examples. It must be pointed out that the following examples are only used to illustrate the present disclosure, not to limit the present disclosure. The experimental methods in the following examples wherein specific conditions are not noted mean conventional methods and conditions, or they can be selected according to product specifications.

The hyzetimibe bulk drug of the present disclosure was provided by Zhejiang Hisun Pharmaceutical Co., Ltd. The hyzetimibe bulk drug is in crystal type I, and the preparation therefor can be found in WO2014036956.

Example 1

A hyzetimibe tablet (aqueous granulation), strength: 10 mg, weighing 100 mg per tablet. The prescription composition (in g) is as follows:

| | |
|---|---|
| hyzetimibe | 10.00 |
| lactose monohydrate 200 mesh | 39.75 |
| microcrystalline cellulose 101 | 39.75 |
| croscarmellose sodium | 5.00 |
| povidone K30 | 2.50 |
| sodium dodecylsulfate | 2.00 |
| magnesium stearate | 1.00 |
| Total | 1000 tablets |

Preparation Method:
1. sieving the hyzetimibe bulk drug (unmicronized), lactose monohydrate 200 mesh, microcrystalline cellulose 101, sodium dodecylsulfate, and croscarmellose sodium through a 40 mesh screen, and then premixing;
2. dissolving povidone K30 in purified water (30% of prescription amount) for later use;
3. adding the povidone K30 solution of step 2 into the mixture of step 1, granulating, and sizing wet particles using a 1.0 mm screen;
4. placing the wet particles in a fluidized bed set at an inlet air temperature of 55-65° C., and drying;
5. sizing through the 1.0 mm screen;
6. adding magnesium stearate and mixing; and
7. tabletting.

Example 2

A hyzetimibe tablet (aqueous granulation), strength: 10 mg, weighing 100 mg per tablet. The prescription composition (in g) is as follows:

| | |
|---|---|
| hyzetimibe | 10.00 |
| lactose monohydrate 200 mesh | 39.75 |
| microcrystalline cellulose 101 | 39.75 |
| croscarmellose sodium | 5.00 |
| povidone K30 | 2.50 |
| sodium dodecylsulfate | 2.00 |
| magnesium stearate | 1.00 |
| total | 1000 tablets |

Preparation Method:
The hyzetimibe bulk drug was pulverized by a jet mill, and the preparation method was the same as in Example 1.

Example 3

A hyzetimibe tablet (alcohol granulation prescription), strength: 10 mg, weighing 200 mg per tablet. The prescription composition (in g) is as follows:

| | |
|---|---|
| hyzetimibe | 10.00 |
| lactose monohydrate 200 mesh | 113.96 |
| microcrystalline cellulose 101 | 60.00 |
| povidone K30 | 4.00 |
| crospovidone XL | 10.00 |
| butylated hydroxytoluene | 0.04 |
| magnesium stearate | 2.00 |
| total | 1000 tablets |

Preparation Method:
1. sieving lactose monohydrate 200 mesh, microcrystalline cellulose 101 and crospovidone XL through a 40 mesh screen, and then premixing;
2. dissolving butylated hydroxytoluene, povidone K30 and hyzetimibe in 85% (w/w) aqueous ethanol solution (35% of prescription amount) for later use as a binder solution;
3. adding the binder solution of step 2 into the mixture of step 1, granulating, and sizing wet particles using a 1.0 mm screen;
4. placing the wet particles in an oven set at a temperature of 40-50° C., and drying;
5. sizing through the 1.0 mm screen;
6. adding magnesium stearate and mixing; and
7. tabletting.

Example 4

A hyzetimibe tablet, strength: 5 mg, weighing 100 mg per tablet. The prescription composition (in g) is as follows:

| | |
|---|---|
| hyzetimibe | 5.00 |
| lactose monohydrate 200 mesh | 57.98 |
| microcrystalline cellulose 101 | 30.00 |
| povidone K30 | 1.00 |
| crospovidone XL | 5.00 |
| butylated hydroxytoluene | 0.02 |
| magnesium stearate | 1.00 |
| total | 1000 tablets |

The preparation method was the same as Example 3.

Example 5

A hyzetimibe tablet, strength: 5 mg, weighing 100 mg per tablet. The prescription composition (in g) is as follows:

| | |
|---|---|
| hyzetimibe | 5.00 |
| lactose monohydrate 200 mesh | 53.98 |
| microcrystalline cellulose 101 | 30.00 |
| povidone K30 | 5.00 |
| crospovidone XL | 5.00 |
| butylated hydroxytoluene | 0.02 |
| magnesium stearate | 1.00 |
| total | 1000 tablets |

The preparation method was the same as Example 3.

Example 6

A hyzetimibe tablet, strength: 5 mg, weighing 100 mg per tablet. The prescription composition (in g) is as follows:

| | |
|---|---|
| hyzetimibe | 5.00 |
| lactose monohydrate 200 mesh | 56.98 |
| microcrystalline cellulose 101 | 30.00 |
| povidone K30 | 2.00 |
| crospovidone XL | 5.00 |
| butylated hydroxytoluene | 0.02 |
| magnesium stearate | 1.00 |
| total | 1000 tablets |

The preparation method was the same as Example 3.

Example 7

A hyzetimibe tablet, strength: 5 mg, weighing 100 mg per tablet. The prescription composition (in g) is as follows:

| | |
|---|---|
| hyzetimibe | 5.00 |
| lactose monohydrate 200 mesh | 54.98 |
| microcrystalline cellulose 101 | 30.00 |
| povidone K30 | 2.00 |
| sodium dodecylsulfate | 2.00 |
| crospovidone XL | 5.00 |
| butylated hydroxytoluene | 0.02 |
| magnesium stearate | 1.00 |
| total | 1000 tablets |

Preparation Method:
1. sieving lactose monohydrate 200 mesh, microcrystalline cellulose 101, crospovidone XL, and sodium dodecylsulfate through a 40 mesh screen, and then premixing;
2. dissolving butylated hydroxytoluene, povidone K30 and hyzetimibe in 85% (w/w) aqueous ethanol solution (35% of prescription amount) for later use as a binder solution;
3. adding the binder solution of step 2 into the mixture of step 1, granulating, and sizing wet particles using a 1.0 mm screen;
4. placing the wet particles in an oven set at a temperature of 40-50° C., and drying;
5. sizing through the 1.0 mm screen;
6. adding magnesium stearate and mixing; and
7. tabletting.

Example 8

A hyzetimibe tablet, strength: 10 mg, 200 mg per tablet. The prescription composition (in g) is as follows:

| | |
|---|---|
| hyzetimibe | 10.00 |
| lactose monohydrate 200 mesh | 109.96 |
| microcrystalline cellulose 101 | 60.00 |
| povidone K30 | 4.00 |
| sodium dodecylsulfate | 4.00 |
| crospovidone XL | 10.00 |
| butylated hydroxytoluene | 0.04 |
| magnesium stearate | 2.00 |
| total | 1000 tablets |

The preparation method was the same as Example 7.

Example 9

A hyzetimibe tablet, strength: 20 mg, 400 mg per tablet. The prescription composition (in g) is as follows:

| | |
|---|---|
| hyzetimibe | 20.00 |
| lactose monohydrate 200 mesh | 219.92 |
| microcrystalline cellulose 101 | 120.00 |
| povidone K30 | 8.00 |
| sodium dodecylsulfate | 8.00 |
| crospovidone XL | 20.00 |
| butylated hydroxytoluene | 0.08 |
| magnesium stearate | 4.00 |
| total | 1000 tablets |

The preparation method was the same as Example 7.

Example 10

A hyzetimibe tablet, strength: 20 mg, 400 mg per tablet. The prescription composition (in g) is as follows:

| | |
|---|---|
| hyzetimibe | 20.00 |
| lactose monohydrate 200 mesh | 220.00 |
| microcrystalline cellulose 101 | 120.00 |
| povidone K30 | 8.00 |
| sodium dodecylsulfate | 8.00 |
| crospovidone XL | 20.00 |
| magnesium stearate | 4.00 |
| total | 1000 tablets |

Preparation Method:
1. sieving lactose monohydrate 200 mesh, microcrystalline cellulose 101, crospovidone XL, and sodium dodecylsulfate through a 40 mesh screen, and then premixing;
2. dissolving povidone K30 and hyzetimibe in 85% (w/w) aqueous ethanol solution (35% of prescription amount) for later use as a binder solution;
3. adding the binder solution of step 2 into the mixture of step 1, granulating, and sizing wet particles using a 1.0 mm screen;
4. placing the wet particles in an oven set at a temperature of 40-50° C., and drying;
5. sizing through the 1.0 mm screen;
6. adding magnesium stearate and mixing; and
7. tabletting.

Example 11

A hyzetimibe tablet, strength: 20 mg, 100 mg per tablet. The prescription composition (in g) is as follows:

| | |
|---|---|
| hyzetimibe | 20.00 |
| lactose monohydrate 200 mesh | 47.98 |
| microcrystalline cellulose 101 | 25.27 |
| povidone K30 | 1.68 |
| crospovidone XL | 4.21 |
| butylated hydroxytoluene | 0.02 |
| magnesium stearate | 0.84 |
| total | 1000 tablets |

Preparation Method:
1. sieving lactose monohydrate 200 mesh, microcrystalline cellulose 101 and crospovidone XL through a 40 mesh screen, and then premixing;
2. dissolving butylated hydroxytoluene, povidone K30 and hyzetimibe in 85% (w/w) aqueous ethanol solution for later use as a binder solution;

3. adding the binder solution of step 2 into the mixture of step 1, granulating, and sizing wet particles using a 1.0 mm screen;
4. placing the wet particles in an oven set at a temperature of 40-50° C., and drying;
5. sizing through the 1.0 mm screen;
6. adding magnesium stearate and mixing; and
7. tabletting.

Example 12

Hyzetimibe placebo, 400 mg per tablet. The prescription composition (in g) is as follows:

| | |
|---|---|
| microcrystalline cellulose 101 | 20.00 |
| lactose monohydrate 200 mesh | 219.92 |
| microcrystalline cellulose 101 | 120.00 |
| povidone K30 | 8.00 |

-continued

| | |
|---|---|
| sodium dodecylsulfate | 8.00 |
| crospovidone XL | 20.00 |
| butylated hydroxytoluene | 0.08 |
| magnesium stearate | 4.00 |
| total | 1000 tablets |

Preparation Method:
1. sieving lactose monohydrate 200 mesh, microcrystalline cellulose 101, crospovidone XL, and sodium dodecylsulfate through a 40 mesh screen, and then premixing;
2. dissolving butylated hydroxytoluene and povidone K30 in 85% (w/w) aqueous ethanol solution (35% of prescription amount) for later use as a binder solution;
3. adding the binder solution of step 2 into the mixture of step 1, granulating, and sizing wet particles using a 1.0 mm screen;
4. placing the wet particles in an oven set at a temperature of 40-50° C., and drying;
5. sizing through the 1.0 mm screen;
6. adding magnesium stearate and mixing; and
7. tabletting.

Test Example 1

After oral administration of tablets prepared in Example 1 and Example 2 to male Beagle dogs, the pharmacokinetic characteristics thereof in dogs were investigated. The data from the animal experiment is shown in Table 1 and Table 2.

TABLE 1

Pharmacokinetic parameters of hyzetimibe after oral administration of 10 mg/kg hyzetimibe tablets of Example 1 (aqueous granulation) to male Beagle dogs

| Pharmacokinetic parameters | Measured value | | | | | | Mean value (ng/ml) | Standard deviation | Coefficient of variation (%) |
|---|---|---|---|---|---|---|---|---|---|
| | Dog#7-8337022 | Dog#8-8338354 | Dog#9-8336807 | Dog#10-8337404 | Dog#11-8341924 | Dog#12-8343552 | | | |
| $T_{max}$ (hr) | 12.0 | 4.00 | 24.0 | 8.00 | 8.00 | 12.0 | 11.3 | 6.89 | 60.8 |
| $C_{max}$ (ng/ml) | 1.61 | 1.48 | 2.69 | 4.60 | 0.757 | 1.53 | 2.11 | 1.37 | 64.7 |
| $AUC_{last}$ (hr*ng/ml) | 26.9 | 12.5 | 48.0 | 55.9 | 13.2 | 32.6 | 31.5 | 17.8 | 56.4 |

TABLE 2

Pharmacokinetic parameters of hyzetimibe after oral administration of 10 mg/kg hyzetimibe tablets of Example 2 (micronization and aqueous granulation prescription) to male Beagle dogs

| Pharmacokinetic parameters | Measured value | | | | | | Mean value (ng/ml) | Standard deviation | Coefficient of variation (%) |
|---|---|---|---|---|---|---|---|---|---|
| | Dog#1-8337022 | Dog#2-8338354 | Dog#3-8336807 | Dog#4-8337404 | Dog#5-8341924 | Dog#6-8343552 | | | |
| $T_{max}$ (hr) | 2.00 | 2.00 | 12.0 | 24.0 | 2.00 | 24.0 | 11.0 | 10.8 | 98.1 |
| $C_{max}$ (ng/ml) | 49.4 | 3.29 | 2.91 | 1.30 | 1.35 | 5.43 | 10.6 | 19.1 | 180 |
| $AUC_{last}$ (hr*ng/ml) | 424 | 20.4 | 38.0 | 34.2 | 15.4 | 106 | 106 | 159 | 150 |

Conclusion: The tablets of Example 2 (comprising micronizing the hyzetimibe bulk drug) can significantly improve the bioavailability of hyzetimibe in vivo.

Test Example 2

After oral administration of tablets prepared in Example 3 to male Beagle dogs, the pharmacokinetic characteristics thereof in dogs were investigated. The data from the animal experiment is shown in Table 3.

TABLE 3

Pharmacokinetic parameters of hyzetimibe after oral administration of 10 mg/kg hyzetimibe tablets of Example 3 (alcohol granulation prescription) to male Beagle dogs

| Pharmacokinetic parameters | Measured value | | | | | | Mean value (ng/ml) | Standard deviation | Coefficient of variation (%) |
|---|---|---|---|---|---|---|---|---|---|
| | Dog#1-8337022 | Dog#2-8338354 | Dog#3-8336807 | Dog#4-8337404 | Dog#5-8341924 | Dog#6-8343552 | | | |
| $T_{max}$(hr) | 2.00 | 2.00 | 12.0 | 12.0 | 24.0 | 12.0 | 10.7 | 8.16 | 76.5 |
| $C_{max}$ (ng/ml) | 73.7 | 2.29 | 2.71 | 3.38 | 1.79 | 7.52 | 15.2 | 28.7 | 189 |
| $AUC_{last}$ (hr*ng/ml) | 570 | 24.7 | 46.8 | 57.0 | 38.7 | 140 | 146 | 212 | 145 |

As compared to the tablets of Examples 1 and 2 (both aqueous granulation prescription for hyzetimibe), the tablets of Example 3 (alcohol granulation prescription) can result in a higher bioavailability of hyzetimibe in vivo.

Test Example 3

Study on the Stability of Hyzetimibe Tablets (Strength: 10 mg)

After the tablets prepared in Example 3 was subjected to aluminum-plastic packaging, they were packaged in a blank middle sealing bag (containing 2 g of desiccant therein) and placed under the condition of temperature of 25±2° C. and humidity (RH) of 60%±5% for stability study. The test results are shown in Table 4.

TABLE 4

Stability data of hyzetimibe tablets (strength: 10 mg)
Storage condition: 25 ± 2° C., RH 60% ± 5%
Packaging condition: aluminum plastic panel plus blank middle sealing bag, containing 2 g of desiccant therein

| | Test Items | 0 month | 3 months | 6 months | 9 months | 12 months | 18 months | 24 months |
|---|---|---|---|---|---|---|---|---|
| Content (%) | Hyzetimibe | 102.0 | 104.3 | 102.8 | 101.7 | 102.5 | 102.7 | 102.9 |
| Related Substances (%) | Single Largest Impurity (Hyzetimibe) | 0.05 | 0.08 | 0.05 | 0.06 | 0.06 | 0.06 | 0.04 |
| | Total Impurities (Hyzetimibe) | 0.10 | 0.19 | 0.15 | 0.17 | 0.17 | 0.20 | 0.22 |
| Dissolution (%) | Hyzetimibe | 83 | 83 | 85 | 84 | 80 | 83 | 88 |

The results show that after storage at 25±2° C. and RH 60% 5% for 24 months, the content and dissolution of the hyzetimibe tablet (10 mg) did not change significantly, and the impurities increased slightly, indicating that the sample was stable.

Test Example 4

Stability Data from the Stability Study on Hyzetimibe Tablets (Strength: 5 mg)

After the tablets prepared in Example 6 were subject to aluminum-plastic packaging, they were packaged in a blank middle sealing bag (containing 2 g of desiccant therein) and placed under the condition of temperature of 25±2° C. and humidity (RH) of 60%±5% for stability study. The test results are shown in Table 5.

TABLE 5

Stability data of hyzetimibe tablets (strength: 5 mg)
Storage condition: 25 ± 2° C., RH 60% ± 5%
Packaging condition: aluminum plastic panel plus blank middle sealing bag,
containing 2 g of desiccant therein

| Test items | | 0 month | 3 months | 6 months | 9 months | 12 months | 18 months | 24 months |
|---|---|---|---|---|---|---|---|---|
| Content (%) | Hyzetimibe | 101.7 | 100.6 | 100.8 | 101.1 | 99.7 | 101.0 | 101.6 |
| Related substances (%) | Single largest impurity (hyzetimibe) | 0.05 | 0.07 | 0.05 | 0.06 | 0.06 | 0.07 | 0.06 |
| | Total impurities (hyzetimibe) | 0.09 | 0.18 | 0.14 | 0.18 | 0.17 | 0.18 | 0.21 |
| Dissolution (%) | Hyzetimibe | 85 | 83 | 84 | 82 | 87 | 84 | 85 |

The results show that after storage at 25±2° C. and RH 60%±5% for 24 months, the content and dissolution of the hyzetimibe tablet (5 mg) do not change significantly, and the impurities increase slightly, indicating that the sample is stable.

Test Example 5

Stability Data from the Stability Study on Hyzetimibe Tablets (Strength: 10 mg)

After the tablets prepared in Example 8 were subject to aluminum-plastic packaging, they were packaged in a blank middle sealing bag (containing 2 g of desiccant therein) and placed under the condition of temperature of 25±2° C. and humidity (RH) of 60%±5% for stability study. The test results are shown in Table 6.

TABLE 6

Stability data of hyzetimibe tablets (strength: 10 mg)
Storage condition: 25 ± 2° C., RH 60% ± 5%
Packaging condition: aluminum plastic panel plus blank middle sealing bag,
containing 2 g of desiccant therein

| Test items | | 0 month | 3 months | 6 months | 9 months | 12 months | 18 months | 24 months | 36 months |
|---|---|---|---|---|---|---|---|---|---|
| Content (%) | Hyzetimibe | 99.6 | 101.0 | 98.5 | 99.4 | 97.8 | 98.7 | 99.6 | 100.9 |
| Related substances (%) | Single largest impurity (hyzetimibe) | 0.11 | 0.12 | 0.15 | 0.11 | 0.11 | 0.11 | 0.11 | 0.12 |
| | Total impurities (hyzetimibe) | 0.11 | 0.16 | 0.22 | 0.15 | 0.16 | 0.15 | 0.18 | 0.23 |
| Dissolution (%) | Hyzetimibe | 86 | 85 | 85 | 88 | 87 | 88 | 87 | 87 |

The results show that after storage at 25±2° C. and RH 60% 5% for 36 months, the content and dissolution of the hyzetimibe tablet (10 mg) did not change significantly, and the impurities increased slightly, indicating that the sample was stable.

Test Example 6

Stability Data from the Stability Study on Hyzetimibe Tablets (Strength: 20 mg)

After the tablets prepared in Example 9 were subject to aluminum-plastic packaging, they were packaged in a blank middle sealing bag (containing 2 g of desiccant therein) and placed under the condition of temperature of 25±2° C. and humidity (RH) of 60% 5% for stability study. The test results are shown in Table 7.

TABLE 7

Stability data of hyzetimibe tablets (strength: 20 mg)
Storage condition: 25 ± 2° C., RH 60% ± 5%
Packaging condition: aluminum plastic panel plus blank middle sealing bag,
containing 2 g of desiccant therein

| Test items | | 0 month | 3 months | 6 months | 9 months | 12 months | 18 months | 24 months | 36 months |
|---|---|---|---|---|---|---|---|---|---|
| Content (%) | Hyzetimibe | 101.6 | 100.5 | 102.7 | 101.9 | 101.8 | 100.9 | 102.3 | 101.6 |
| Related substances (%) | Single largest impurity (hyzetimibe) | 0.27 | 0.25 | 0.28 | 0.26 | 0.27 | 0.27 | 0.27 | 0.26 |
| | Total impurities (hyzetimibe) | 0.54 | 0.55 | 0.70 | 0.61 | 0.76 | 0.76 | 0.76 | 0.71 |
| Dissolution (%) | Hyzetimibe | 86 | 89 | 89 | 89 | 89 | 88 | 89 | 88 |

The results show that after storage at 25±2° C. and RH 60% 5% for 36 months, the content and dissolution of the hyzetimibe tablet (20 mg) did not change significantly, and the impurities increased slightly, indicating that the sample was stable.

Test Example 7

Stability Data of Hyzetimibe Tablets without BHT

After the tablets of Example 9 and Example 10 were subject to aluminum-plastic packaging, they were packaged in a blank middle sealing bag (containing 2 g of desiccant therein) and placed under the condition of temperature of 40±2° C. and humidity (RH) of 75%±5% for stability study. The test results are shown in Table 8.

TABLE 8

Stability data of hyzetimibe tablets (strength: 20 mg)

| | Test items | 0 month | 3 months |
|---|---|---|---|
| Tablets prepared in Example 10 | Specific impurities | 0.05 | 0.18 |
| Tablets prepared in Example 9 | Specific impurities | 0.00 | 0.03 |

Test Example 8

Effect of Sodium Dodecylsulfate (SDS) on the Dissolution of Hyzetimibe Tablets

Dissolution test: paddle method, dissolution medium: 0.1 N hydrochloric acid solution containing 0.5% SDS, rotary speed: 50 rpm, medium volume: 900 mL The dissolution of the tablets of Example 3 and Example 8 were measured respectively, and the results are shown in Table 9.

TABLE 9

Comparison of dissolution data of hyzetimibe tablets (strength: 10 mg)

| | Time (min) | | | | | | | |
|---|---|---|---|---|---|---|---|---|
| | 5 | 10 | 15 | 20 | 30 | 45 | 60 | 90 |
| Example 3(%) | 40 | 62 | 73 | 79 | 84 | 89 | 91 | 95 |
| Example 8(%) | 55 | 73 | 81 | 86 | 90 | 93 | 95 | 96 |

The results show that the tablets of Example 8 dissolve faster than that of Example 3, indicating that sodium dodecylsulfate comprised in prescription can promote the dissolution of hyzetimibe.

Test Example 9

Study on the Crystal Form of Hyzetimibe

Figure 1:
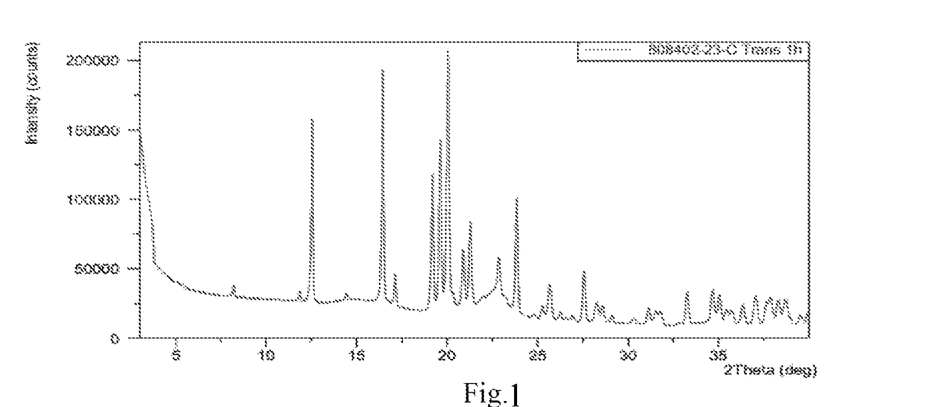
FIG. 1: XRD pattern of hyzetimibe placebo.
Figure 2:
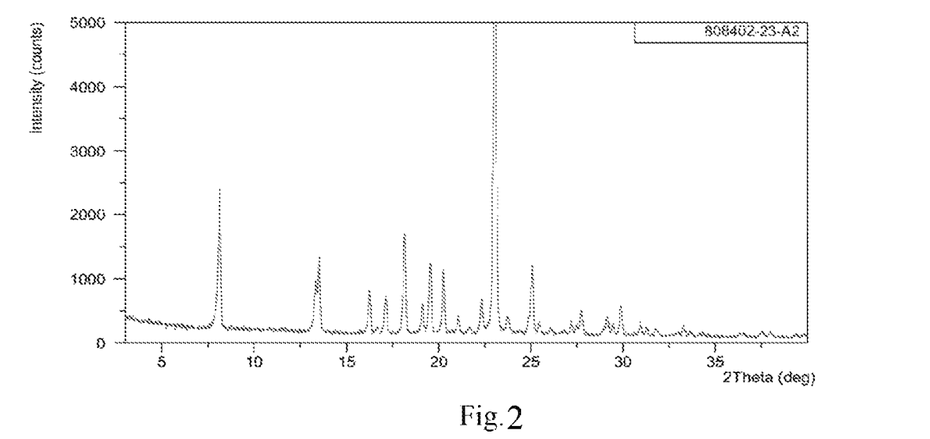
FIG. 2: XRD pattern of hyzetimibe bulk drug (crystal form I).
Figure 3:
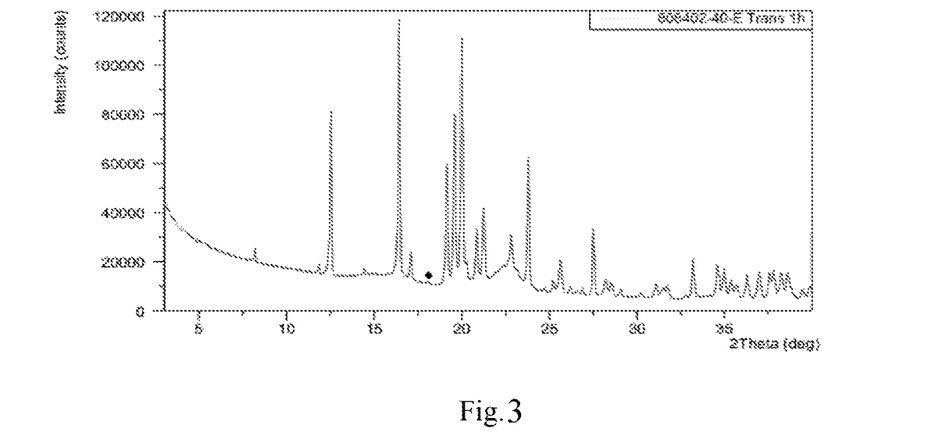
FIG. 3: XRD pattern of a mixture of hyzetimibe placebo and hyzetimibe bulk drug (crystal form I).
Figure 4:
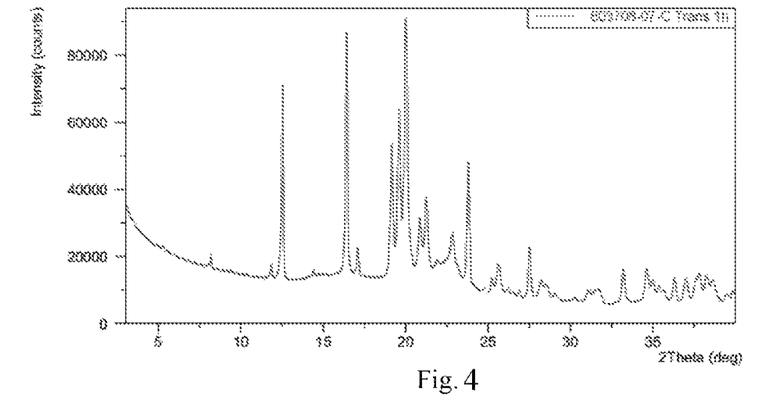
FIG. 4: XRD pattern of a hyzetimibe tablet with an API concentration of 20% at 0 month.
Figure 5:
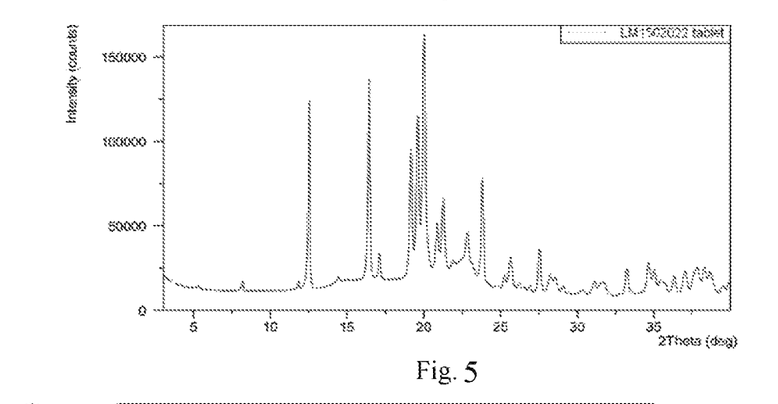
FIG. 5: XRD pattern of a hyzetimibe tablet with an API concentration of 20% at 3 months.

The hyzetimibe placebo and hyzetimibe bulk drug (crystal form I) were mixed at a weight ratio of 98:2. The resulting mixture was subjected to X-ray diffraction (XRD) test to obtain a XRD pattern of the mixture of hyzetimibe placebo and hyzetimibe bulk drug (crystal form I) (see FIG. 3). Then, the XRD pattern of FIG. 3 was compared with that of the hyzetimibe placebo (see FIG. 1) and that of the hyzetimibe bulk drug (crystal form I) (see FIG. 2). At the position of 18° in FIG. 3, a characteristic peak of hyzetimibe crystal form I was detected, and the detection limit of the XRD detection equipment for hyzetimibe crystal form I was judged as 2%, indicating that when the crystal form I in tablets accounts for equal to or more than 2% of the total tablet weight, the crystal form I would be detected. Hyzetimibe tablets with an API content of 20% prepared in Example 11 were subjected to XRD detection, and no peak at 18° was found (see FIG. 4), indicating that in the tablets prepared according to the method of Example 11, the bulk drug present in crystal form I was less than 2% of the tablet weight, that is, in the tablets of Example 11, more than 18% by tablet weight of bulk drug was present in an amorphous form. Therefore, it can be determined that in the tablets of Example 11, hyzetimibe in an amorphous form accounts for more than 90% of the total amount of the bulk drug. Stability of the tablets of Example 11 (hyzetimibe 20 mg, alcohol granulation) was investigated under accelerated conditions (temperature 40±2° C., humidity (RH) 75%±5%), and the results are shown in FIG. 5 and FIG. 6:

FIG. 5 shows that the content of amorphous hyzetimibe is still above 90% under accelerated conditions for 3 months.

Figure 6:
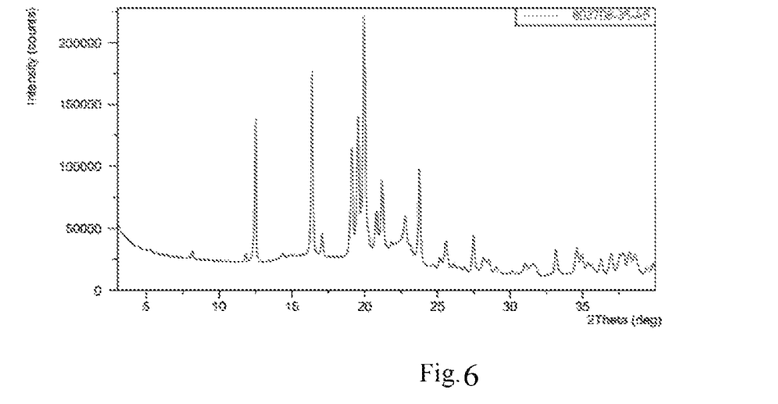
FIG. 6: XRD pattern of a hyzetimibe tablet with an API concentration of 20% at 9 months.

FIG. 6 shows that the content of amorphous hyzetimibe is still above 90% under accelerated conditions for 9 months.

The invention claimed is:

1. An hyzetimibe tablet, comprising hyzetimibe, a filler, a binder, a disintegrating agent and a lubricant, wherein hyzetimibe accounts for 1-20% by weight of the tablet wherein the binder is povidone.

2. The hyzetimibe tablet according to claim 1, wherein the filler is at least one of lactose, microcrystalline cellulose and pregelatinized starch; the disintegrating agent is at least one of crospovidone and croscarmellose sodium; and the lubricant is at least one of magnesium stearate and talc.

3. The hyzetimibe tablet according to claim 1, further comprising a stabilizer and/or surfactant.

4. The hyzetimibe tablet according to claim 3, wherein the stabilizer is at least one of butylated hydroxyanisole and butylated hydroxytoluene; and the surfactant is at least one of sodium dodecylsulfate and polysorbate.

5. The hyzetimibe tablet according to claim 1, comprising 30-60% by weight of lactose, 20-60% by weight of microcrystalline cellulose, 1-5% by weight of povidone, 1-10% by weight of crospovidone or croscarmellose sodium, 0-0.1% by weight of butylated hydroxytoluene, 0-5% by weight of sodium dodecylsulfate, and 0.5-2% by weight of magnesium stearate.

6. The hyzetimibe tablet according to claim 5, comprising 0.005-0.1% by weight of butylated hydroxytoluene.

7. The hyzetimibe tablet according to claim 5, comprising 1-5% by weight of sodium dodecylsulfate.

8. The hyzetimibe tablet according to claim 1, which can be prepared by granulating using water, alcohol, acetone or a similar solvent, or a mixture thereof, and then tabletting.

9. The hyzetimibe tablet according to claim 1, comprising a hyzetimibe solid dispersion comprising hyzetimibe and povidone.

10. A hyzetimibe solid dispersion composition, comprising hyzetimibe and povidone.

11. A hyzetimibe tablet, comprising the hyzetimibe solid dispersion composition of claim 10.

12. A method for preparing a hyzetimibe solid formulation, comprising using the hyzetimibe solid dispersion composition of claim 10.

13. The method according to claim 12, wherein the solid formulation is selected from the group consisting of tablet, capsule, granule and powder.

14. A method for preparing the hyzetimibe solid dispersion composition of claim 10, comprising the following step:
dissolving hyzetimibe in an organic solvent comprising povidone.

15. The preparation method according to claim 14, further comprising pouring or spraying the obtained hyzetimibe solution into adjuvant materials.

16. The preparation method according to claim 14, wherein the organic solvent is selected from the group consisting of ethanol, isopropanol, and a mixture thereof with water.

17. A method for preparing the hyzetimibe tablet of claim 8, comprising the following steps:
(1) mixing hyzetimibe with lactose, microcrystalline cellulose, sodium dodecylsulfate and croscarmellose sodium homogeneously;
(2) dissolving povidone in water;
(3) adding the povidone solution of step (2) into the mixture of step (1), granulating, drying, and sizing; and
(4) mixing the sized particles in step (3) with magnesium stearate homogeneously, and tabletting.

18. The preparation method for the hyzetimibe tablet according to claim 17, wherein hyzetimibe used in the preparation is hyzetimibe crystal form I.

19. The preparation method for the hyzetimibe tablet according to claim 17, wherein hyzetimibe used in the preparation has a particle size of 1 µm≤D90≤100 µm, and preferably 1 µm≤D90≤50 µm.

20. A method for preparing the hyzetimibe tablet according to claim 8, comprising the following steps:
(1) mixing lactose, microcrystalline cellulose, sodium dodecylsulfate and crospovidone homogeneously, or mixing lactose, microcrystalline cellulose and crospovidone homogeneously;
(2) dissolving hyzetimibe, povidone and butylated hydroxytoluene in an alcohol solvent, or dissolving hyzetimibe and povidone in an alcohol solvent;
(3) adding the solution obtained in step (2) into the mixture obtained in step (1), granulating, drying, and sizing; and
(4) mixing the particles obtained in step (3) with magnesium stearate homogeneously, and tabletting.

21. The preparation method for the hyzetimibe tablet according to claim 20, wherein the alcohol solvent used in the preparation method is an aqueous ethanol solution, preferably in a concentration of ≥60% (w/w), more preferably ≥75% (w/w), and most preferably 80-90% (w/w), and in an amount of 30-50% (w/w) of prescription amount, and more preferably 35-45% (w/w) of prescription amount.

22. The preparation method for the hyzetimibe tablet according to claim 20, wherein in the preparation method, the weight ratio of hyzetimibe to povidone is in a range of 10:1-1:1, and more preferably 5:1-5:3.

23. The preparation method for the hyzetimibe tablet according to claim 20, wherein the granulating includes granulating using a high-speed stirring pelletizer or fluidized bed.

24. The preparation method for the hyzetimibe tablet according to claim 20, wherein in the prepared hyzetimibe tablet, more than 90% of hyzetimibe is present in an amorphous form.

25. A hyzetimibe tablet prepared by the preparation method according to claim 17.

26. The hyzetimibe tablet according to claim 1, comprising 5-20 mg of hyzetimibe in each dosage unit.

27. The hyzetimibe tablet according to claim 26, comprising 5 mg, 10 mg or 20 mg of hyzetimibe in each dosage unit.

28. The hyzetimibe tablet according to claim 26, comprising, in each dosage unit, 20-250 mg of lactose, 20-200 mg of microcrystalline cellulose, 1-10 mg of croscarmellose sodium or 5-30 mg of crospovidone, 1-15 mg of povidone K30, 0-0.2 mg of butylated hydroxytoluene, 0-15 mg of sodium dodecylsulfate, and 0.5-10 mg of magnesium stearate.

* * * * *